United States Patent
Shintaku et al.

(10) Patent No.: US 6,740,770 B2
(45) Date of Patent: May 25, 2004

(54) CRYSTAL OF BICALUTAMIDE AND PRODUCTION METHOD THEREOF

(75) Inventors: Tetsuya Shintaku, Osaka (JP); Tadashi Katsura, Osaka (JP); Nobushige Itaya, Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 33 days.

(21) Appl. No.: 10/362,410

(22) PCT Filed: Dec. 13, 2002

(86) PCT No.: PCT/JP02/13058
§ 371 (c)(1),
(2), (4) Date: Feb. 24, 2003

(87) PCT Pub. No.: WO03/053920
PCT Pub. Date: Jul. 3, 2003

(65) Prior Publication Data
US 2003/0191337 A1 Oct. 9, 2003

(30) Foreign Application Priority Data

Dec. 13, 2001 (JP) .......................... 2001-380686
Jun. 6, 2002 (JP) .......................... 2002-166213

(51) Int. Cl.$^7$ .......................... C07C 255/50
(52) U.S. Cl. .......................... 558/413; 558/414
(58) Field of Search .......................... 558/413, 414

(56) References Cited

U.S. PATENT DOCUMENTS

| | | | |
|---|---|---|---|
| 4,636,505 A | 1/1987 | Tucker | |
| 6,562,994 B2 * | 5/2003 | Chen et al. | ........... 558/413 |

FOREIGN PATENT DOCUMENTS

| | | |
|---|---|---|
| EP | 0 002 892 A1 | 7/1979 |
| WO | WO 01/00608 A1 | 1/2001 |
| WO | WO 01/28990 A2 | 4/2001 |
| WO | WO 01/34563 A1 | 5/2001 |
| WO | WO 02/24638 A1 | 3/2002 |

OTHER PUBLICATIONS

Tucker et al., "Nonsteroidal Antiandrogens. Synthesis and Structure–Activity Relationships of 3–Substituted Derivatives of 2 Hydroxypropionanilides," *J. Med. Chem.*, 31 (5), 954–959 (1988).

Hauptschein et al., "Trifluoromethyl Derivatives of Hydroxybenzoic Acids and Related Compounds," *J. Am. Chem. Soc.*, 76, 1051–1054 (1954).

\* cited by examiner

*Primary Examiner*—Cecilia Tsang
*Assistant Examiner*—Ebenezer Sackey
(74) *Attorney, Agent, or Firm*—Leydig, Voit & Mayer, Ltd.

(57) ABSTRACT

The present invention relates to a crystal of bicalutamide having a defined form, as well as economical and industrially practical production methods of bicalutamide and a crystal thereof, which are superior in environmental benignity and safety.

Accordingly, the present invention provides a production method of bicalutamide represented by the formula (I):

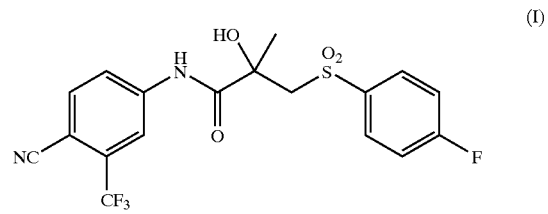

(I)

which includes at least a step of reacting a compound represented by the formula (3):

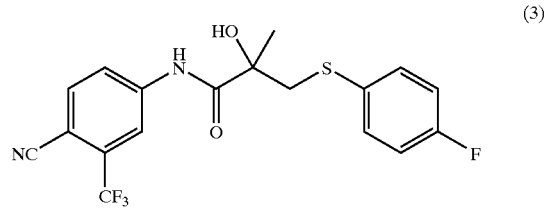

(3)

with an oxidizing agent, a production method of a crystal of bicalutamide, as well as a crystal form of bicalutamide as defined by X-ray diffraction (XRD) or solid $^{13}$C NMR measurement.

5 Claims, 1 Drawing Sheet

CRYSTAL OF BICALUTAMIDE AND PRODUCTION METHOD THEREOF

TECHNICAL FIELD

The present invention relates to a crystal of bicalutamide having a defined form and a production method thereof.

BACKGROUND ART

Bicalutamide represented by the formula (I):

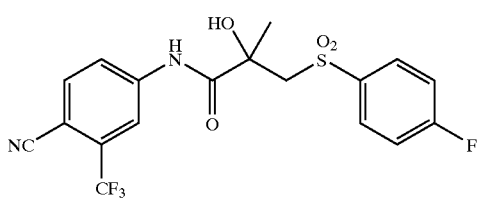

(hereinafter sometimes referred to as compound of the formula (I) or compound (I) in the present specification) has been reported to be useful as a compound having an anti-angrogenic action (JP-B-4-32061, U.S. Pat. No. 4,636,505 and WO01/34563). As a synthetic method of the compound of the formula (I), for example, a method comprising a reaction of 4'-cyano-3-(4-fluorophenylthio)-2-hydroxy-2-methyl-3'-trifluoromethylpropionanilide represented by the formula (3):

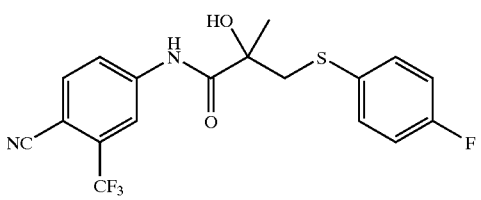

(hereinafter sometimes referred to as compound of the formula (3) or compound (3)) in methylene chloride solution with m-chloroperbenzoic acid is known (Howard Tucker et al, J. Med. Chem., Vol. 31, 954–959 (1988), and WO01/28990). In this method, methylene chloride is used as a solvent. Halogenated organic solvents such as methylene chloride and the like are generally harmful for human body, and the possibility of carcinogenicity thereof has been suggested. Furthermore, they may produce dioxin during waste treatments. Halogenated organic solvents such as methylene chloride and the like are associated with the problems of economic burden for the cost of waste treatment after use, and of corrosion of incinerator used for the waste treatment.

In recent years, "Green Chemistry" has been drawing attention as one of the measures for risk reduction of chemical substances, and industrial application of environmentally benign type chemical reactions (or reaction not using substances potentially harmful to human body and the environment (e.g., halogen-containing substances etc.) as much as possible, and not emitting them as much as possible) has become a very important object. From this aspect, the above-mentioned production method using methylene chloride as an organic solvent is not entirely a preferable production method of bicalutamide. Therefore, the development of a production method of bicalutamide, which is superior in environmental benignity, is desired.

In addition, the above-mentioned method uses m-chloroperbenzoic acid as an oxidizing agent. m-Chloroperbenzoic acid is highly explosive and is not preferable for industrial processes. Furthermore, m-chloroperbenzoic acid is expensive and poses an economic problem.

Accordingly, industrial practice of the above-mentioned method at a large scale gives rise to the problems not only in environmental benignity, but also safety and economic aspect, due to the use of a halogenated organic solvent as the solvent and of m-chloroperbenzoic acid as the oxidizing agent.

At the moment, as a synthetic method of bicalutamide, which is free of the use of m-chloroperbenzoic acid as an oxidizing agent, the method described in, for example, WO01/00608 is known. According to this method, compound (3) is oxidized with aqueous hydrogen peroxide as an oxidizing agent, in acetic acid or formic acid, for the synthesis of bicalutamide. Thus, this method is considered to be environmentally, economically and industrially superior. In this method, however, synthesis of precursor compound (3) requires many steps (at least 4 steps), which makes this method not an economically and industrially superior synthetic method for the total synthesis of bicalutamide. Furthermore, this method includes steps using a halogenated solvent (e.g., methylene chloride etc.) for the synthesis of compound (3). Thus, it is difficult to say that this method is sufficiently environmentally conscious.

As a synthetic method of bicalutamide free of use of m-chloroperbenzoic acid as an oxidizing agent, a method described in WO02/24638 is also known. The method described in WO02/24638 includes adding aqueous hydrogen peroxide to compound (3), cooling (e.g., −55° C.) the mixture, and adding trifluoroacetic anhydride to the mixture to give bicalutamide. However, this method uses expensive trifluoroacetic anhydride as a reagent, and requires cooling when trifluoroacetic anhydride is added, and is not an economically superior method. Furthermore, because of the corrosive and hygroscopic property of trifluoroacetic anhydride, the method is unsuitable for the industrial production of bicalutamide.

Accordingly, the development of an economical and industrially practical production method of bicalutamide, which is superior in environmental benignity and safety, is desired in this field.

For efficient granulation of a crystal in the field of the production of pharmaceutical drugs, it is desirable that the form of the crystal be defined. However, the form of the crystal of bicalutamide is not defined in any of the above-mentioned references, and therefore, those of ordinary skill in the art of the production of pharmaceutical drugs strongly desire provision of bicalutamide crystals having a defined form.

DISCLOSURE OF THE INVENTION

It is therefore an object of the present invention to provide bicalutamide having a defined crystal form, as well as an economical and industrially practical production method of bicalutamide and a crystal thereof, which is superior in environmental benignity and safety.

As a result of intensive studies by the present inventors in an attempt to solve the above-mentioned problems, they have found that bicalutamide having high purity can be produced in a large amount by reacting a compound of the above-mentioned formula (3) with aqueous hydrogen peroxide, which is an oxidizing agent, using ethyl acetate as a solvent, in the presence of sodium tungstate (or a solvate thereof), phenylphosphonic acid and a phase transfer catalyst. This method is superior in environmental benignity, economic aspect and safety, and is industrially practicable. The present inventors have also found that mono-perphthalic acid as an oxidizing agent prepared from phthalic anhydride and hydrogen peroxide is highly effective as an oxidizing agent for oxidation of olefin to epoxide, and for oxidation of thioether to sulfone, based on which fact they have found production methods of bicalutamide and a crystal thereof, which are mainly based on oxidation reactions and which are capable of finally deriving bicalutamide, which is a sulfone, sequentially via olefin, epoxide and thioether (compound (3)) from a simple starting material, as well as the specific form of the crystal of bicalutamide, which resulted in the completion of the present invention. Accordingly, the present invention provides the following.

[1] A production method of bicalutamide represented by the formula (I):

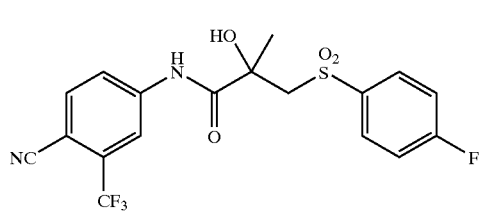

(I)

which comprises a step of reacting a compound represented by the formula (1):

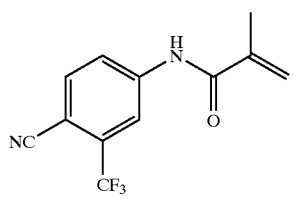

(1)

with mono-perphthalic acid to give a compound represented by the formula (2):

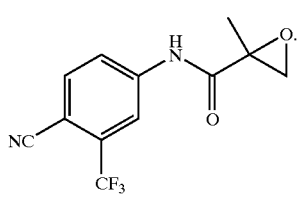

(2)

[2] The production method of the above-mentioned [1], further comprising use of methanesulfonyl chloride.

[3] A production method of bicalutamide represented by the formula (I):

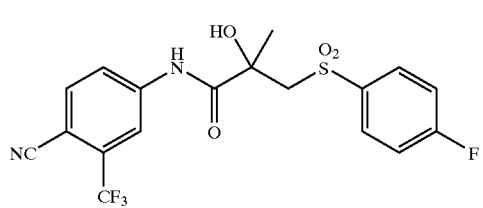

(I)

which comprises reacting a compound represented by the formula (3):

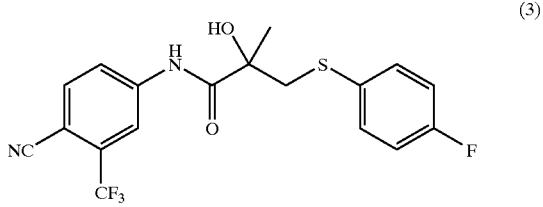

(3)

with mono-perphthalic acid.

[4] The production method of any of the above-mentioned [1] to [3], which comprises preparing the mono-perphthalic acid from phthalic anhydride and hydrogen peroxide.

[5] A production method of bicalutamide represented by the formula (I):

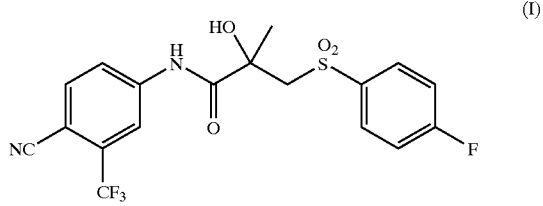

(I)

which comprises the following Steps (A)–(C):

(A) a step of reacting a compound represented by the formula (1):

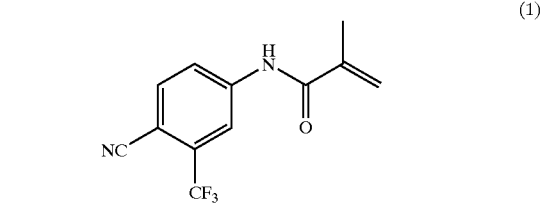

(1)

with mono-perphthalic acid to give a compound represented by the formula (2):

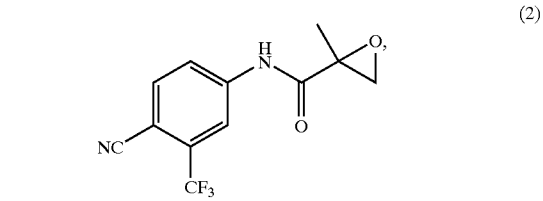

(2)

(B) a step of reacting the compound of the formula (2) obtained in Step (A) with 4-fluorothiophenol to give a compound represented by the formula (3):

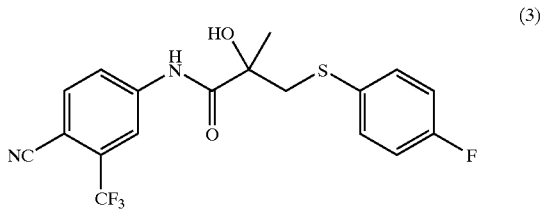

(3)

(C) a step of reacting the compound of the formula (3) obtained in Step (B) with mono-perphthalic acid to give bicalutamide.

[6] The production method of the above-mentioned [5], wherein the Step (A) further comprises use of methanesulfonyl chloride.

[7] The production method of the above-mentioned [5] or [6], which comprises a step of preparing the mono-perphthalic acid from phthalic anhydride and hydrogen peroxide.

[8] A production method of bicalutamide represented by the formula (I):

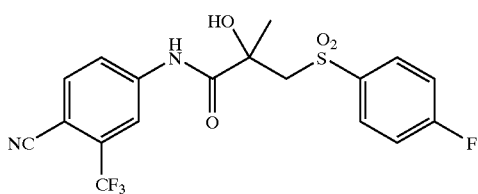

which comprises reacting a compound represented by the formula (3):

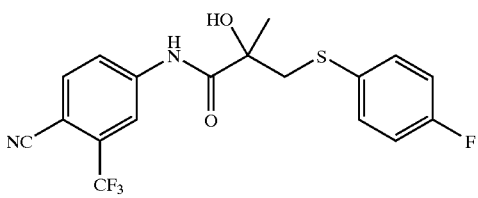

with aqueous hydrogen peroxide, in the presence of sodium tungstate or a solvate thereof, phenylphosphonic acid and a phase transfer catalyst, in ethyl acetate.

[9] The production method of the above-mentioned [8], wherein the amount of hydrogen peroxide to be used is a 3 to 6-fold molar amount of the compound represented by the formula (3).

[10] The production method of the above-mentioned [8] or [9], wherein the amount of sodium tungstate or a solvate thereof to be used is 0.5–5 mol % of the compound represented by the formula (3).

[11] The production method of any of the above-mentioned [8] to [10], wherein the amount of phenylphosphonic acid to be used is 0.5–5 mol % of the compound represented by the formula (3).

[12] The production method of any of the above-mentioned [8] to [11], wherein the amount of the phase transfer catalyst to be used is 0.5–5 mol % of the compound represented by the formula (3).

[13] The production method of any of the above-mentioned [8] to [12], wherein sodium tungstate or a solvate thereof is sodium tungstate dihydrate and the phase transfer catalyst is tetrabutylammonium bromide.

[14] The production method of any of the above-mentioned [1] to [13], further comprising
(I) a step of preparing a solution containing bicalutamide,
(II) a step of adding, where necessary, a hydrocarbon solvent to the solution obtained in Step (I), and
(III) a step of cooling the solution obtained in Step (I) or (II) to allow precipitation of a crystal of bicalutamide.

[15] The production method of the above-mentioned [14], wherein the Step (I) comprises concentration of a solution.

[16] The production method of the above-mentioned [15], wherein the solution is a solution of bicalutamide in ethyl acetate.

[17] The production method of the above-mentioned [14], wherein the solution obtained in Step (II) is a solution of bicalutamide in a mixed solvent of ethyl acetate and heptane.

[18] The production method of the above-mentioned [14], wherein the Steps (I)–(III) are respectively the following Steps (i)–(iii):
(i) a step of adding ethyl acetate to bicalutamide,
(ii) a step of adding, where necessary, a hydrocarbon solvent selected from hexane and heptane to the solution obtained in Step (i), and
(iii) a step of cooling the solution obtained in Step (i) or (ii) to allow precipitation of a crystal of bicalutamide.

[19] The production method of the above-mentioned [18], wherein, in Step (i), 1.0 ml–10 ml of ethyl acetate is added per 1 g of bicalutamide, and, in Step (ii), 1.5 ml–5 ml of the hydrocarbon solvent is added per 1 g of bicalutamide.

[20] The production method of the above-mentioned [18], wherein, in Step (i), 2 ml–6 ml of ethyl acetate is added per 1 g of bicalutamide, and, in Step (ii), 1.5 ml–3.5 ml of the hydrocarbon solvent is added per 1 g of bicalutamide.

[21] The production method of any of the above-mentioned [18] to [20], wherein the solution obtained in Step (i) is at 50° C.–70° C.

[22] The production method of any of the above-mentioned [18] to [21], wherein, in Step (ii), the hydrocarbon solvent is added at a rate of 1.0 ml/min–4.0 ml/min per 1 g of bicalutamide.

[23] The production method of any of the above-mentioned [18] to [22], wherein, in Step (iii), the solution obtained in Step (i) or (ii) is cooled to 0° C.–30° C.

[24] A production method of a crystal of bicalutamide, comprising the following Steps (I)–(III):
(I) a step of preparing a solution containing bicalutamide,
(II) a step of adding, where necessary, a hydrocarbon solvent to the solution obtained in Step (I), and
(III) a step of cooling the solution obtained in Step (I) or (II) to allow precipitation of a crystal of bicalutamide.

[25] The production method of the above-mentioned [24], wherein the Step (I) comprises concentration of a solution.

[26] The production method of the above-mentioned [25], wherein the solution is a solution of bicalutamide in ethyl acetate.

[27] The production method of the above-mentioned [24], wherein the solution obtained in Step (II) is a solution of bicalutamide in a mixed solvent of ethyl acetate and heptane.

[28] The production method of the above-mentioned [24], wherein the Steps (I)–(III) are respectively the following Steps (i)–(iii):
(i) a step of adding ethyl acetate to bicalutamide,
(ii) a step of adding, where necessary, a hydrocarbon solvent selected from hexane and heptane to the solution obtained in Step (i), and
(iii) a step of cooling the solution obtained in Step (i) or (ii) to allow precipitation of a crystal of bicalutamide.

[29] The production method of the above-mentioned [28], wherein, in Step (i), 1.0 ml–10 ml of ethyl acetate is added per 1 g of bicalutamide, and, in Step (ii), 1.5 ml–5 ml of the hydrocarbon solvent is added per 1 g of bicalutamide.

[30] The production method of the above-mentioned [28], wherein, in Step (i), 2 ml–6 ml of ethyl acetate is added per 1 g of bicalutamide, and, in Step (ii), 1.5 ml–3.5 ml of the hydrocarbon solvent is added per 1 g of bicalutamide.

[31] The production method of any of the above-mentioned [28] to [30], wherein the solution obtained in Step (i) is at 50° C.–70° C.

[32] The production method of any of the above-mentioned [28] to [31], wherein, in Step (ii), the hydrocarbon solvent is added at a rate of 1.0 ml/min–4.0 ml/min per 1 g of bicalutamide.

[33] The production method of any of the above-mentioned [28] to [32], wherein, in Step (iii), the solution obtained in Step (i) or (ii) is cooled to 0° C.–30° C.

[34] A crystal of bicalutamide having peaks of δ at 177.08, 168.16, 164.69, 142.31, 136.58, 133.09, 124.80, 118.50, 116.16, 104.68, 75.56, 67.14 and 29.23 ppm in $^{13}$C-NMR.

[35] A crystal of bicalutamide having a particle size distribution of $D_{10}$ 9.5 μm, $D_{50}$ 30.3 μm and $D_{90}$ 65.9 μm.

[36] A crystal of bicalutamide having a mean particle size of 30.3 μm.

[37] A crystal of bicalutamide having peaks at 2θ of 6.2, 12.3, 19.1, 23.9, 24.7 and 31.1 in X-ray diffraction.

[38] A crystal of bicalutamide having peaks at 2θ of 12.18, 16.8, 18.9, 23.72 and 24.64 in X-ray diffraction.

DETAILED DESCRIPTION OF THE INVENTION

Figure 1:
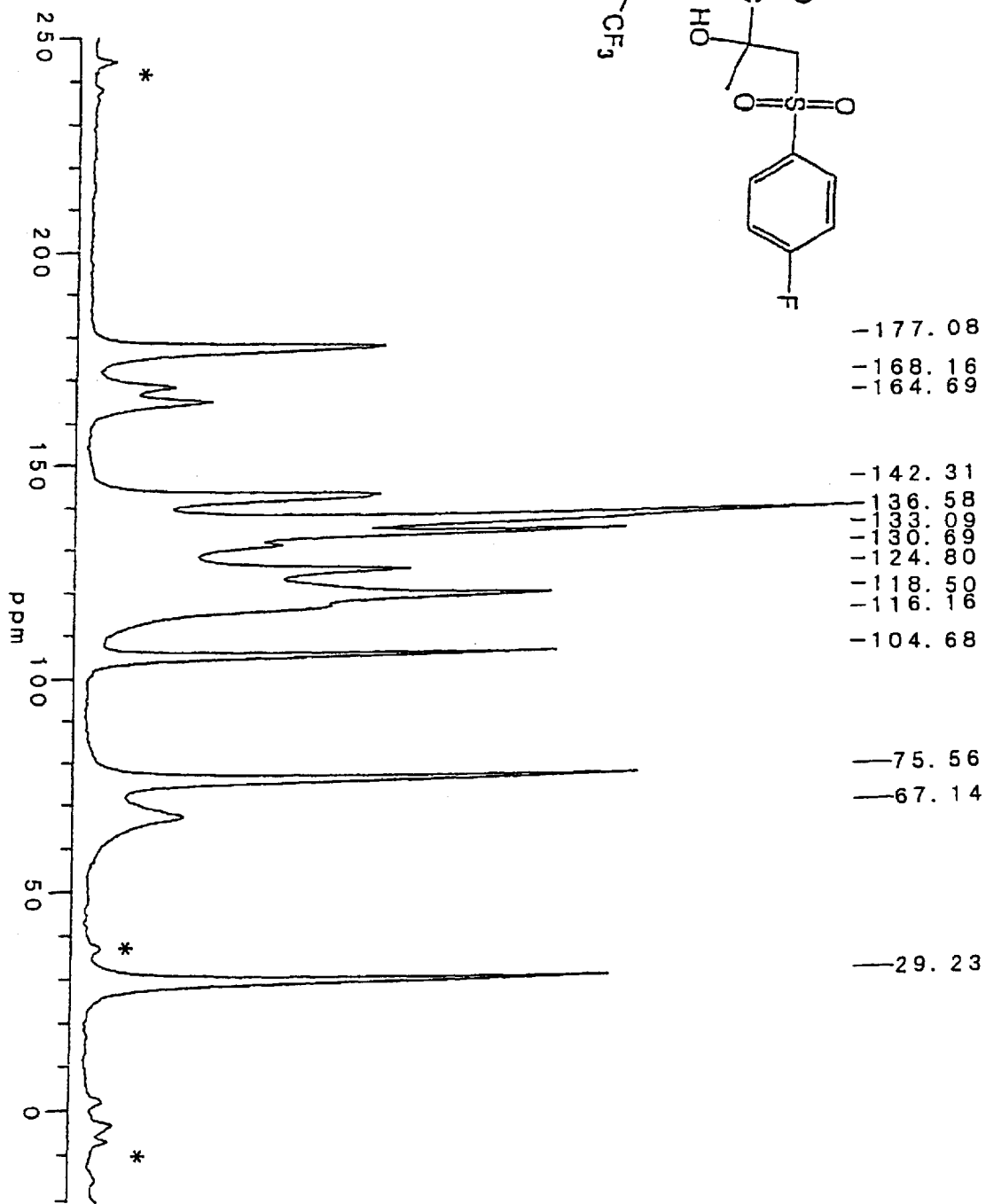
FIG. 1 is a chart showing solid $^{13}$C VACP/MAS NMR spectrum of a crystal of bicalutamide, wherein the symbol * shows a spinning side band.

The present invention is explained in detail by referring to the following Scheme 1.

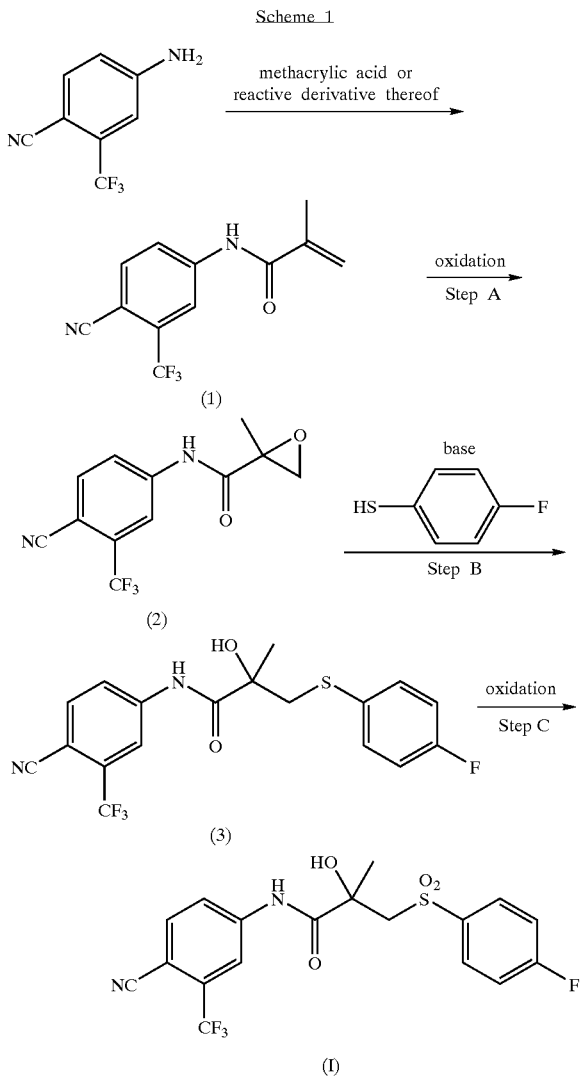

In the present invention, the total synthesis of bicalutamide is started using 4-cyano-3-(trifluoromethyl)aniline as a starting material. 4-Cyano-3-(trifluoromethyl)aniline may be commercially available or may be separately synthesized and used, because its structure is simple (J. Am. Chem. Soc., 76, 1051–1054 (1954); see EP2892). By subjecting 4-cyano-3-(trifluoromethyl)aniline to condensation reaction with methacrylic acid or its reactive derivative (e.g., methacryloyl halide etc., preferably methacryloyl chloride), an olefin compound represented by the above-mentioned formula (1) (hereinafter sometimes referred to as compound (1)) can be obtained. Since methacrylic acid and its reactive derivative are extremely economical as commercially available products and can be easily obtained in large amounts, the condensation reaction may be an industrially and economically effective means. This condensation reaction can be carried out according to conventional amide chemistry. In addition, compound (1) can be used for the next reaction without isolation and/or purification.

Step A and Step C are oxidation steps using an oxidizing agent.

In Step A (oxidation of olefin to epoxide) and Step C (oxidation of thioether to sulfone), mono-perphthalic acid can be used as an oxidizing agent for safe and economical production at an industrial scale.

The mono-perphthalic acid can be easily prepared by reacting phthalic anhydride with hydrogen peroxide.

To be specific, mono-perphthalic acid is prepared by mixing phthalic anhydride and hydrogen peroxide in an almost equimolar amount or an amount not less than the equimolar amount in a suitable solvent in the presence or absence of a base. Preferably, a slightly excess amount of hydrogen peroxide is used relative to phthalic anhydride. To be specific, hydrogen peroxide is used in a proportion of 1.0 mol–1.5 mol, preferably 1.0 mol–1.3 mol, relative to 1 mol of phthalic anhydride.

Phthalic anhydride is used as a starting material for the synthesis of mono-perphthalic acid, because phthalic anhydride is economical, free of hygroscopic property and is easy to handle.

From the aspect of easy handling, hydrogen peroxide to be used is preferably aqueous hydrogen peroxide. The aqueous hydrogen peroxide to be used has a concentration of generally 20%–50%, preferably 30%–35%. Aqueous hydrogen peroxide having a concentration of 30%–35% is preferable, because it is associated with less possibility of explosion and is commercially available and economical.

Examples of the base include sodium carbonate, sodium hydrogencarbonate, potassium carbonate, sodium hydroxide and the like. From the economic aspect, sodium carbonate is preferable.

The amount of the base to be used is generally 1.0 mol–1.3 mol, preferably 1.0 mol–1.2 mol, per 1 mol of phthalic anhydride.

As the solvent to be used, water and the like can be exemplified. Of these, deionized water is preferable because it does not contain metals possibly having a catalytic activity to decompose hydrogen peroxide, and from the aspects of solubility of hydrogen peroxide therein and from the economic aspect.

The amount of the solvent to be used is generally 2 ml–5 ml, preferably 3 ml–4 ml, per 1 g of phthalic anhydride.

The reaction temperature is generally –5° C. to 5° C., preferably –5° C. to 0° C.

While the reaction time varies depending on the reagents to be used and the reaction temperature, it is generally 0.5 hr–2.0 hr, preferably 0.5 hr–0.75 hr.

After the completion of the reaction, the reaction system may be neutralized, as necessary, with an acid such as sulfuric acid (preferably 98% sulfuric acid) and the like, and isolated and/or purified by conventional work-up.

Since mono-perphthalic acid-can be prepared by one-pot, it can be used for the subsequent oxidation reaction (i.e., the above-mentioned Step A and Step C) without isolation and/or purification, which in turn reduces the total number of steps for the total synthesis of bicalutamide.

In the following, Steps A, B and C are explained in detail.

Step A

In Step A, olefin compound (1) is oxidized to derive an epoxy compound represented by the formula (2) (hereinafter sometimes referred to as compound (2)).

When mono-perphthalic acid is used as an oxidizing agent, in Step A, mono-perphthalic acid, which is an oxidizing agent, is added to compound (1) in a suitable reaction solvent.

A reaction solvent suitable for the oxidation reaction in Step A is exemplified by toluene, chlorobenzene, ethyl acetate and the like, of which ethyl acetate is preferable from the aspect of solubility of compound (1) therein.

The amount of the reaction solvent to be used is generally 0.5 ml–10 ml, preferably 0.7 ml–5 ml, more preferably 1.0 ml–5 ml, still more preferably 2 ml–5 ml, yet still more preferably 2.5 ml–4 ml, per 1 g of compound (1).

The amount of the mono-perphthalic acid to be used is generally 1.2 mol–3.5 mol, preferably 1.5 mol–3.0 mol, more preferably 1.8 mol–2.5 mol, per 1 mol of compound (1).

As a method for adding mono-perphthalic acid, dropwise addition of mono-perphthalic acid solution is preferable from the aspect of easy addition, safety and operability. When mono-perphthalic acid solution is added dropwise, the solution may be dropwise added in two or more portions.

As a solvent suitable for the preparation of mono-perphthalic acid solution, for example, ethyl acetate, ethers (e.g., diethyl ether etc.) and the like are mentioned, of which ethyl acetate is preferable from the aspect of safety. It is desirable to use the same solvent as the above-mentioned reaction solvent.

The concentration of the mono-perphthalic acid solution to be used for the reaction is generally 10 wt %–22 wt %, preferably 12 wt %–19 wt %.

The amount of the solvent to be used for the preparation of mono-perphthalic acid solution is generally 3 ml–10 ml, preferably 3.5 ml–7.5 ml, more preferably 3.5 ml–7 ml, per 1 g of mono-perphthalic acid.

When the mono-perphthalic acid solution is added dropwise, the rate of dropwise addition depends on the concentration of the solution for dropwise addition and temperature of the solution for dropwise addition or of the solution to which the mono-perphthalic acid solution is added dropwise, but generally 0.5 ml/min–4.0 ml/min, 1 ml/min–4 ml/min, preferably 1.5 ml/min–3.0 ml/min, per 1 g of compound (1).

When a mono-perphthalic acid solution is added dropwise, the temperature of the solution for dropwise addition is generally 0° C.–35° C., preferably 10° C.–30° C.

When a mono-perphthalic acid solution is added dropwise, the temperature of the solution to which the mono-perphthalic acid solution is added dropwise is generally 20° C.–60° C., preferably 40° C.–55° C., more preferably 50° C.–55° C.

The reaction temperature is generally 20° C.–60° C., preferably 45° C.–55° C., more preferably 50° C.–55° C.

While the reaction time varies depending on the reaction temperature and other reaction conditions, it is generally 5 hr–15 hr, preferably 6 hr–9 hr.

The progress of the reaction can be confirmed by LC (Liquid Chromatography).

After the reaction is completed, as necessary, the reaction system may be made to be weak basic (e.g., pH≅8) with a base such as potassium hydroxide, potassium carbonate and the like, and may be isolated and/or purified by a conventional work-up.

It is also possible to use the reaction mixture in the next step without isolation and/or purification of the reaction mixture.

When mono-perphthalic acid is prepared in the absence of a base, mono-perphthalic acid may be prepared from hydrogen peroxide and excess amount of phthalic anhydride, in the reaction system of Step A, at the above-mentioned reaction temperature.

While the presence of a by-product represented by the following formula (A) (hereinafter sometimes referred to as by-product (A)) can be confirmed by LC, the by-product (A) may be converted to compound (2) at this time (see the following Scheme 2).

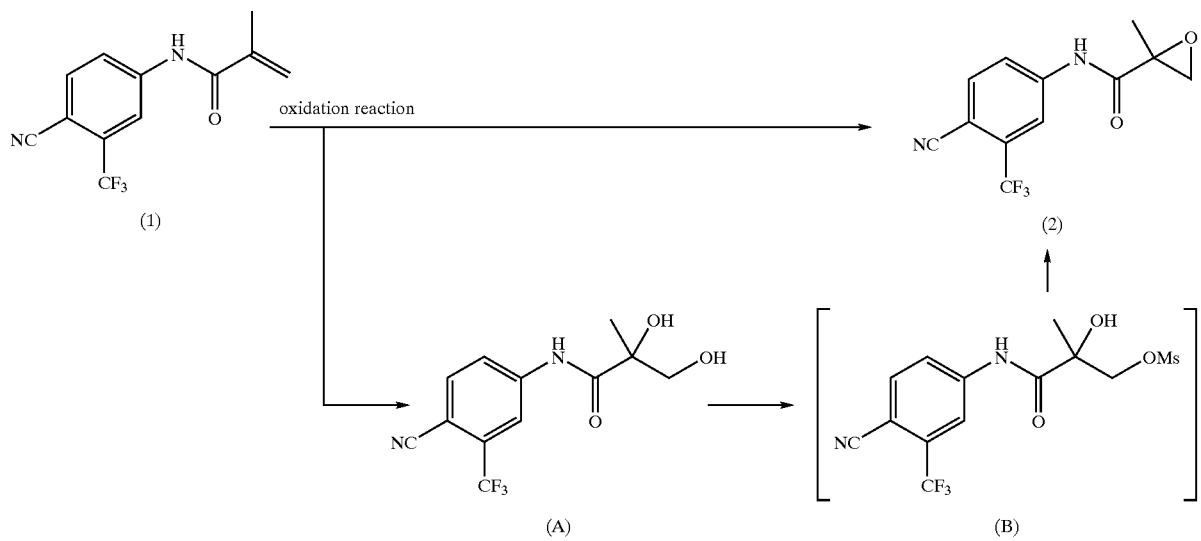

Scheme 2

In the Scheme, Ms in the compound represented by the formula (B) (hereinafter sometimes referred to as compound (B)) represents methanesulfonyl group.

In Scheme 2, the by-product (A) from the above-mentioned oxidation reaction can be mesylated, in the presence of a base, with methanesulfonyl chloride (MsCl) in a suitable solvent, and, via compound (B), converted to compound (2) via ring closure (epoxidation of diol form).

Via compound (B), the by-product (A) can be removed efficiently, and compound (B) can be converted easily to compound (2), as a result of which bicalutamide can be obtained in stable quality and yield.

As a suitable solvent, for example, toluene, THF, ethyl acetate and the like can be mentioned, of which toluene is preferable from the aspect of economic aspect and THF is preferable from the aspect of solubility. In addition, a mixed solvent of the above-mentioned solvents may be used.

The amount of the solvent to be used is generally 1.5 ml–10 ml, preferably 1.5 ml–7 ml, per 1 g of compound (1).

As the base, for example, amines such as triethylamine, pyridine and the like, and the like can be mentioned, of which triethylamine is preferable from the economic aspect and for easy handling.

The amount of the base to be used is generally 0.1 mol–0.6 mol, preferably 0.15 mol–0.6 mol, per 1 mol of compound (1).

The amount of the methanesulfonyl chloride to be used is generally 0.05 mol–0.3 mol, preferably 0.06 mol–0.3 mol, per 1 mol of compound (1).

The base and methanesulfonyl chloride are preferably added sequentially. The base and methanesulfonyl chloride may be each added in two or more portions.

When the base and methanesulfonyl chloride are added, the temperature of the solution for dropwise addition is generally 0° C.–30° C., preferably 0° C.–25° C., for both.

When the base and methanesulfonyl chloride are added, the temperature of the solution to which they are added dropwise is generally 0° C.–15° C., preferably 0° C.–10° C., for both.

The reaction temperature is generally 0° C.–15° C., preferably 0° C.–10° C.

While the reaction time varies depending on the reaction temperature and other reaction conditions, it is generally 0.25 hr–0.75 hr, preferably 0.30 hr–0.70 hr.

The reaction for converting a diol form to an epoxy form may be started from the crude reaction mixture from the oxidation reaction in the above-mentioned Step A (namely, a mixture containing compound (2) and by-product (A)).

By converting the by-product (A) to compound (2), the quality and yield of the total synthesis of bicalutamide can be improved.

The progress of the reaction can be traced by LC.

The reaction mixture can be used for the next step without isolation and/or purification.

Step B

In Step B, the compound of the formula (2) obtained in the above-mentioned Step A and 4-fluorothiophenol are reacted in the presence or absence of a base to give compound (3).

In Step B, nucleophilisity of 4-fluorophenol is increased due to the presence of a base in the reaction system, which in turn improves the purity and yield of the obtained compound (3).

In Step B, the base is, for example, sodium hydride, sodium hydroxide, sodium carbonate, potassium hydroxide and the like. From the economic aspect, sodium hydroxide is preferable. As sodium hydroxide, aqueous sodium hydroxide solution is preferable from the easiness of the handling. A commercially available aqueous sodium hydroxide solution may be used as it is, or used after dilution. The concentration of the aqueous sodium hydroxide solution to be used is generally 5 wt %–20 wt %, preferably 15 wt %–20 wt %.

In Step B, from the aspect of operability, a base is preferably added in advance to a 4-fluorothiophenol solution in a suitable reaction solvent (more preferably dropwise addition of a solution containing a base), and compound (2) is added to the mixture (more preferably dropwise addition of a solution containing compound (2)).

As a suitable reaction solvent, polar solvents such as toluene, THF, t-butanol and the like are mentioned, of which THF is preferable from the aspect of solubility of compound (2) therein.

The amount of the reaction solvent to be used is generally 1 ml–40 ml, preferably 2 ml–20 ml, per 1 g of compound (2).

The amount of the base to be used is generally 1.0 mol–1.3 mol, preferably 1.0 mol–1.2 mol, per 1 mol of 4-fluorothiophenol.

4-Fluorothiophenol may be added dropwise after diluting with a 0.5 to 1.5-fold volume of a solvent (e.g., hydrocarbon solvents such as toluene and the like, and the like) relative to 4-fluorothiophenol to be used.

The temperature for addition of a base is generally 0° C.–30° C., preferably 0° C.–20° C.

The temperature for addition of Compound (2) is generally 0° C.–15° C., preferably 0° C.–10° C.

When compound (2) is added dropwise as a solution, the solvent may be, for example, non-protonic solvents such as THF and the like, of which THF is preferable from the aspect of solubility of compound (2) therein. The same solvent as the above-mentioned reaction solvent is desirable. The amount of the solvent to be used is generally 1 ml–10 ml, preferably 2 ml–6 ml, per 1 g of compound (2).

The reaction temperature is generally 0° C.–30° C., preferably 0° C.–20° C.

While the reaction time varies depending on the reaction temperature and other reaction conditions, it is generally 1 hr–20 hr, preferably 2 hr–15 hr.

When a base is used in Step B, a base other than the above-mentioned may be used (e.g., amines such as triethylamine and the like, and the like). As the base, triethylamine is preferable from the aspect of the economic aspect. In addition, when a base such as triethylamine and the like is used, the above-mentioned reaction solvent such as toluene and the like may or may not be used as a solvent.

The amount of the base to be used is generally 0.3 mol–1.0 mol, preferably 0.3 mol–0.8 mol, per 1 mol of compound (1) or compound (2).

The amount of the 4-fluorothiophenol to be used is generally 1.0 mol–1.7 mol, preferably 1.0 mol–1.5 mol, per 1 mol of compound (1) or compound (2).

When a base is used in Step B, from the aspect of operability, 4-fluorothiophenol is preferably added in advance to compound (2) (preferably dropwise addition), and a base is added to the mixture. 4-Fluorothiophenol may be diluted with a solvent (e.g., toluene and the like) and the dilute solution may be added (preferably dropwise addition). Where necessary, 4-fluorothiophenol may be further added in two or more portions.

The temperature for addition of 4-fluorothiophenol is generally 0° C.–20° C., preferably 0° C.–15° C.

The temperature for addition of a base is generally 0° C.–35° C., preferably 0° C.–30° C.

The reaction temperature is generally 0° C.–60° C., preferably 0° C.–50° C.

While the reaction time varies depending on the reaction temperature and other reaction conditions, it is generally 9 hr–48 hr, preferably 10 hr–24 hr.

The reaction mixture may be used in the next step without isolation and purification.

After the reaction is completed, a conventional work-up is conducted, and where necessary, isolation and/or purification may be applied.

Step C

In Step C, sulfide compound (3) is oxidized to derive bicalutamide (I). The oxidation in Step C of the present invention is preferably that using mono-perphthalic acid or hydrogen peroxide as an oxidizing agent.

The oxidation in Step C using mono-perphthalic acid as an oxidizing agent is explained in the following.

In Step C, mono-perphthalic acid, which is an oxidizing agent, is added to compound (3) in a suitable reaction solvent.

The reaction solvent suitable for oxidation reaction in Step C is preferably ethyl acetate from the aspect of operability.

The amount of the solvent to be used is generally 1 ml–20 ml, preferably 1.5 ml–10 ml, preferably 1 ml–3 ml, more preferably 1.5 ml–2.5 ml, per 1 g of compound (3).

The amount of the mono-perphthalic acid to be used is generally 2.1 mol–5 mol, preferably 2.2 mol–4.5 mol, preferably 3 mol–5 mol, more preferably 3.5 mol–4.5 mol, per 1 mol of compound (3).

As a method for adding mono-perphthalic acid, dropwise addition of mono-perphthalic acid solution is preferable from the aspect of easy addition, safety and operability. When mono-perphthalic acid solution is added dropwise, the solution may be dropwise added in two or more portions.

As a solvent suitable for the preparation of mono-perphthalic acid solution, for example, ethyl acetate, ethers (e.g., diethyl ether etc.) and the like are mentioned, of which ethyl acetate is preferable from the aspect of safety. It is desirable to use the same solvent as the above-mentioned reaction solvent.

The concentration of the mono-perphthalic acid solution to be used for the reaction is generally 10 wt %–22 wt %, preferably 12 wt %–19 wt %.

The amount of the solvent to be used for the preparation of mono-perphthalic acid solution is generally 3 ml–10 ml, preferably 3.5 ml–7.5 ml, more preferably 3.5 ml–7 ml, per 1 g of mono-perphthalic acid.

When the mono-perphthalic acid solution is added dropwise, the rate of dropwise addition depends on the concentration of the solution for dropwise addition and temperature of the solution for dropwise addition or of the solution to which the mono-perphthalic acid solution is added dropwise, but generally 1 ml/min–4 ml/min, preferably 1.5 ml/min–3.0 ml/min, per 1 g of compound (3).

When a mono-perphthalic acid solution is added dropwise, the temperature of the solution for dropwise addition is generally 0° C.–30° C., preferably 0° C.–25° C., more preferably 10° C.–25° C.

When a mono-perphthalic acid solution is added dropwise, the temperature of the solution to which the mono-perphthalic acid solution is added dropwise is generally 0° C.–60° C., preferably 0° C.–55° C., more preferably 0° C.–20° C., still more preferably 0° C.–10° C.

The reaction temperature is generally 0° C.–60° C., preferably 0° C.–55° C., more preferably 0° C.–20° C., still more preferably 0° C.–10° C.

While the reaction time varies depending on the reaction temperature and other reaction conditions, it is generally 0.5 hr–24 hr, preferably 0.5 hr–15 hr, more preferably 0.5 hr–5 hr, still more preferably 1 hr–3 hr.

When mono-perphthalic acid is prepared in the absence of a base, mono-perphthalic acid may be prepared from hydrogen peroxide and excess amount of phthalic anhydride at the above-mentioned reaction temperature in the reaction system of Step C.

After the reaction is completed, as necessary, the reaction system may be made to be weak basic (e.g., pH≅8) with a base such as potassium hydroxide, potassium carbonate and the like, and may be isolated and/or purified by a conventional work-up.

The case where hydrogen peroxide is used as an oxidizing agent in Step C is explained in the following.

Bicalutamide can be produced in Step C by reacting compound (3) with aqueous hydrogen peroxide, in the presence of sodium tungstate or a solvate thereof, phenylphosphonic acid and a phase transfer catalyst, in ethyl acetate. To be specific, for example, sodium tungstate or a solvate thereof, phenylphosphonic acid, a phase transfer catalyst and aqueous hydrogen peroxide are charged in a reaction vessel and a solution of compound (3) in ethyl acetate is added thereto. The method for adding a solution of compound (3) in ethyl acetate is not particularly limited, and, for example, dropwise addition, injection and the like are exemplified. A dropwise addition is preferable because the heat of the reaction can be easily removed. The time necessary for the addition is generally 30 min–5 hr, depending on the reaction scale.

When hydrogen peroxide is used as an oxidizing agent, it is essential that ethyl acetate be used as a solvent. This is because ethyl acetate is economical, resists oxidation, and is free of dioxin upon incineration, and further, makes the oxidation reaction proceed well as compared to other solvents. The amount of ethyl acetate to be used is free of any particular limitation as long as stirring is possible. When the amount is generally not less than one-fold weight, preferably 1 to 20-fold weight, more preferably 2 to 10-fold weight of compound (3). When it is 2 to 10-fold weight, the reaction proceeds easily and stirring is easy.

The oxidizing agent to be used in Step C is preferably hydrogen peroxide from the aspect of environmental benignity. This is because hydrogen peroxide produces only water as a by-product after oxidation reaction. Particularly, aqueous hydrogen peroxide is preferable because it is easily handled. Aqueous hydrogen peroxide having a concentration of generally 20–50%, preferably 30–35%, is used. Aqueous hydrogen peroxide having a concentration of 30–35% is preferable, because it is associated with less possibility of explosion and is economical. The amount of use thereof in molar ratio is generally not less than 2.5 relative to compound (3). When it is less than 2.5, the sulfur atom is not sufficiently oxidized and the selectivity toward sulfone or sulfoxide is unpreferably degraded. For production of sulfone with high selectivity, the molar ratio is preferably 3–6.

When hydrogen peroxide is used as an oxidizing agent in Step C, as a reaction catalyst, a catalyst system of sodium tungstate or a solvate thereof-phenylphosphonic acid-phase transfer catalyst is employed. The amount of each of sodium tungstate or a solvate thereof, phenylphosphonic acid and phase transfer catalyst to be used is generally not less than 0.1 mol %, preferably 0.1–10 mol %, more preferably 0.5–5 mol %, of compound (3). When the amount of even one of these catalysts to be used is less than 0.1 mol %, the reaction may not be completed or the reaction time may be prolonged, which is unpreferable. It is preferably 0.5–5 mol % from the aspect of reaction time and economic aspect.

As sodium tungstate and a solvate thereof, for example, sodium tungstate hydrate is preferable, and as sodium tungstate hydrate, sodium tungstate 10 hydrate, sodium tungstate dihydrate and the like are exemplified, with preference given to sodium tungstate dihydrate.

The phase transfer catalyst is not particularly limited and is exemplified by quaternary ammonium salt (e.g., tetrabutylammonium bromide, benzyltrimethylammonium chloride, tetrabutylammonium hydroxide and the like), halogenated phosphonium and the like, with preference given to quaternary ammonium salt. Particularly, the use of tetrabutylammonium bromide, benzyltrimethylammonium chloride or tetrabutylammonium hydroxide is preferable due to easy availability and economic aspect. Particularly, tetrabutylammonium bromide is preferable.

While the reaction temperature is not particularly limited as long as the reaction proceeds, a reaction at the refluxing temperature of ethyl acetate (73–76° C. at atmospheric pressure) is preferable, because the reaction time can be shortened.

The compound (3) can be also obtained according to the method described in, for example, JP-B-4-32061.

Isolation and/or Purification of Bicalutamide

Bicalutamide can be isolated by a conventional method. For example, after the completion of the reaction, it is quenched, an extract solvent (e.g., organic solvent such as ethyl acetate and the like) is added to the reaction mixture, the mixture is stirred and left standing still. After that, the mixture is partitioned and the obtained extract (organic layer) is washed, dried and concentrated. While the isolated bicalutamide can be purified by a conventional method, a crystal of bicalutamide having a higher purity can be obtained in a high yield by precipitating a crystal of bicalutamide from a specific solvent. The production method of a crystal of bicalutamide is explained in detail in the following.

Production Method of Crystals of Bicalutamide

In the present invention, the production method of a crystal of bicalutamide characteristically includes the following Steps I–III:

I. a step of preparing a solution containing bicalutamide,
II. a step of adding, where necessary, a hydrocarbon solvent to the solution obtained in Step I, and
III. a step of cooling the solution obtained in Step I or II to allow precipitation of a crystal of bicalutamide.

Step I

In Step I, a solution containing bicalutamide is prepared.

As a means for preparing a solution containing bicalutamide, for example, addition of a solvent to bicalutamide can be mentioned.

As a solvent, an organic solvents such as ethyl acetate and the like can be exemplified, and from the aspect of solubility, ethyl acetate is preferable.

The amount of the solvent to be added is generally 1.0 ml–10 ml, preferably 1.2 ml–6 ml, more preferably 1.4 ml–6 ml, preferably 2 ml–10 ml, more preferably 2 ml–6 ml, per 1 g of bicalutamide. Particularly, when the solvent is ethyl acetate, it is generally 1.0 ml–10 ml, preferably 1.2 ml–6 ml, more preferably 1.4 ml–6 ml, preferably 2 ml–10 ml, more preferably 2 ml–6 ml, per 1 g of bicalutamide.

A solution containing bicalutamide is heated to generally 40° C.–70° C., preferably 50° C.–70° C. Particularly, when the solvent is ethyl acetate, it is heated to 40° C.–70° C., preferably 50° C.–70° C.

In addition, as a means for preparing a solution containing bicalutamide, concentration of a solution of bicalutamide is exemplified. The solution of bicalutamide to be concentrated is exemplified by a solution wherein bicalutamide is dissolved in an excess amount of the above-mentioned solvent, the extract (an organic layer containing bicalutamide, preferably ethyl acetate layer) explained with regard to the above-mentioned isolation, and the like.

When a solution containing bicalutamide is prepared by concentration in Step I, the solution of bicalutamide is preferably concentrated to the extent free of precipitation of a crystal of bicalutamide. The solution is concentrated to generally 2 ml–10 ml, preferably 2 ml–6 ml, per 1 g of bicalutamide (under atmospheric pressure to reduced pressure). Particularly, when the solvent is ethyl acetate, the solution is preferably concentrated generally to 2 ml–10 ml, 2 ml–6 ml, per 1 g of bicalutamide. After concentration, the concentrated solution is preferably maintained at a temperature free of precipitation of the crystal of bicalutamide. The concentrated solution is maintained generally at 40° C.–80° C., preferably 50° C.–70° C. Particularly, when the solvent is ethyl acetate, the solution is maintained generally at 40° C.–80° C., preferably 50° C.–70° C.

Step II

In Step II, a hydrocarbon solvent is added as necessary to the solution obtained in Step I.

The hydrocarbon solvent to be used in Step II is exemplified by hexane, heptane, petroleum ether and the like, with preference given to hexane and heptane. Of these, heptane is preferable, and n-heptane is particularly preferable.

The temperature of the hydrocarbon solvent to be added is generally 0° C.–50° C., preferably 15° C.–30° C.

When the hydrocarbon solvent is added, the temperature of the solution obtained in the above-mentioned Step I is generally 40° C.–80° C., preferably 50° C.–70° C. Particularly, when the solvent is ethyl acetate, it is 40° C.–70° C., preferably 50° C.–70° C.

The amount of the hydrocarbon solvent to be used in Step II is generally 1.5 ml–5 ml, preferably 2 ml–5 ml, preferably 1.5 ml–3.5 ml, more preferably 2.5 ml–3.5 ml, per 1 g of bicalutamide. Particularly, when the hydrocarbon solvent is heptane, it is generally 1.5 ml–4.0 ml, preferably 1.5 ml–3.5 ml, preferably 2.5 ml–4.0 ml.

In Step II, the rate of addition of the hydrocarbon solvent is generally 1.0 ml/min–5.0 ml/min, preferably 1.0 ml/min–4.0 ml/min, per 1 g of bicalutamide. Particularly, when the hydrocarbon solvent is heptane, it is generally 1.0 ml/min–15 ml/min, preferably 1.0 ml/min–10.0 ml/min, more preferably 1.0 ml/min–5.0 ml/min, still more preferably 1.0 ml/min–4.0 ml/min.

Step III

In Step III, the solution obtained in Step I or II is cooled to allow precipitation of a crystal of bicalutamide.

In Step III, the cooling temperature is 0° C.–40° C., preferably 0° C.–30° C., more preferably 10° C.–30° C.

In Step III, the cooling time is generally 1 hr–24 hr, preferably 1 hr–12 hr, more preferably 1 hr–5 hr, still more preferably 1.5 hr–3 hr.

During cooling in Step III, a solution containing bicalutamide is preferably stirred and then the vessel is left standing as necessary.

As an example of Steps I–III, when a mixed solvent of ethyl acetate and heptane is used for precipitation of a crystal of bicalutamide, the amount thereof to be used is, for example, 3.5–10 ml/g, preferably 4.5–6.5 ml/g, of ethyl acetate relative to compound (3), and, for example, 2–5 ml/g, preferably 2.5–4.5 ml/g, of heptane relative to compound (3).

As an example of Step I–III, when a solution containing bicalutamide is prepared by concentration for precipitation of a crystal of bicalutamide, the organic layer (preferably ethyl acetate layer) obtained by isolation is concentrated to the extent free of precipitation of a product. Then, the concentrated solution of bicalutamide (preferably ethyl acetate solution) is cooled. The cooling temperature is not lower than 50° C. and lower than the reaction temperature, preferably 55° C.–70° C. At this point, the crystal starts to precipitate. To this solution is added (preferably dropwise added) heptane at the same temperature, and then the mixture is further cooled (10° C.–40° C., preferably 15° C.–30° C.), whereby a highly pure crystal of bicalutamide can be obtained.

By precipitating a crystal of bicalutamide as mentioned above, a crystal of bicalutamide having a high purity (98.0%–99.9%) can be obtained in a high yield (98.50%–99.99%).

The crystal polymorphism of the crystal of bicalutamide is evaluated by X-ray diffraction (XRD) and solid $^{13}$C NMR measurement. In addition, particle size distribution and mean particle size of the crystal of bicalutamide are also measured. The crystal of bicalutamide obtained by the production method of the crystal of bicalutamide of the present invention has been clarified to have characteristics shown in the following Examples.

BEST MODE FOR EMBODYING THE INVENTION

The present invention is explained in more detail by referring to the following Reference Examples and Examples, which are not to be construed as limitative.

REFERENCE EXAMPLE 1
Preparation of Mono-Perphthalic Acid

Deionized water (125 ml), $Na_2CO_3$ (31.0 g, 0.25 mol) and 35% $H_2O_2$ (29.15 g, 0.3 mol) are successively charged in a 500 ml four-neck flask, and the mixture was stirred in a dry ice-methanol bath at −5° C.–0° C. Thereto was added phthalic anhydride (37.0 g, 0.25 mol) and the mixture was stirred for 30 min. The bath was removed, ethyl acetate (100 ml) was added to the mixture, and the reaction system was neutralized in a solution obtained by diluting 98% $H_2SO_4$ (15 ml) with deionized water (50 ml). After partitioning, the aqueous layer was extracted with ethyl acetate (60 ml). The obtained organic layer (0.64 g) was taken up and saturated NaI-IPA (isopropyl alcohol) solution (5 ml) and 10% acetic acid-IPA solution (20 ml) were added thereto. The mixture was boiled for 5 min. It was titrated with 0.1N aqueous sodium thiosulfate solution. As a result, mono-perphthalic acid was present in 33.5 g and the yield was 76.9%.

REFERENCE EXAMPLE 2
Synthesis of N-methacryloyl-4-cyano-3-trifluoromethylaniline Using 4-cyano-3-trifluoromethylaniline and methacryloyl chloride as starting materials, the title compound is prepared according to the method described in J. Med. Chem., 1988, 954–959.

EXAMPLE 1
Synthesis of 4-cyano-N-(2,3-epoxy-2-methylpropionyl)-3-trifluoromethylaniline N-Methacryloyl-4-cyano-3-trifluoromethylaniline (13.8 g, 54 mmol) and ethyl acetate (40 ml) were charged in a 300 ml four-neck flask, and the mixture was heated at 50° C.–55° C. A solution of mono-perphthalic acid in ethyl acetate (108.05 g, net 19.82 g, 110 mmol) was added dropwise at a temperature in the range of 50° C.–55° C. over 3.9 hr. After stirring at the above-mentioned temperature for 4.5 hr, a solution of mono-perphthalic acid in ethyl acetate (10.36 g, net 1.90 g, 10.4 mmol) was further added dropwise over 10 min. Then the mixture was stirred for 1 hr and left standing overnight at room temperature. The mixture was adjusted to pH=8 (universal test paper) with 20% aqueous KOH solution and partitioned. The organic layer was washed with deionized water (20 ml) in which $Na_2S_2O_5$ (5.0 g) had been dissolved, dried over $MgSO_4$, decolorized with activated carbon (carborafine 0.5 g), and concentrated under reduced pressure. Toluene (60 ml) was added to the residue and the mixture was heated to 80° C. After cooling to 25° C., the mixture was filtrated to give 4-cyano-N-(2,3-epoxy-2-methylpropionyl)-3-trifluoromethylaniline (11.37 g, yield 77.3%). Purity 98.7%.

Analytical data: $^1$H-NMR (400 MHz, $CDCl_3$): δ=8.40 (s, 1H), 8.01 (d, J=1.8 Hz, 1H), 7.90 (dd, J=8.5, 2.1 Hz, 1H), 7.78 (d, J=8.5 Hz, 1H), 3.00 (s, 1H), 1.68 (s, 3H).

EXAMPLE 2
Synthesis of 4'-cyano-3-(4-fluorophenylthio)-2-hydroxy-2-methyl-3'-trifluoromethylpropionanilide

EXAMPLE 2-1

The title compound is prepared according to the method described in J. Med. Chem., 1988, 954–959.

NaH (1.86 g, 46.5 mmol) and THF (30 ml) were charged in a 200 ml four-neck flask, and the mixture was stirred under ice-cooling. 4-Fluorothiophenol (5.16 g, 40.3 mmol) was diluted with THF (30 ml) and the solution was added dropwise. After stirring for 30 min, 4-cyano-N-(2,3-epoxy-2-methylpropionyl)-3-trifluoromethylaniline (10.37 g, 38.4 mmol) was dissolved in THF (50 ml) and the solution was added dropwise. After stirring for 1 hr, the bath was removed and the mixture was stirred overnight at room temperature. Saturated brine (40 ml) and toluene (40 ml) were added and the mixture was partitioned. Saturated brine (20 ml) and ethyl acetate (80 ml) were added to the organic layer and the mixture was neutralized with 5N HCl. After partitioning, the organic layer was washed twice with saturated brine (30 ml), dried over $MgSO_4$, decolorized with activated carbon (carborafine 0.5 g) and concentrated under reduced pressure to give a residue. Toluene (30 ml) was added to the residue, and n-heptane (22 ml) was added dropwise at a temperature of 70° C.–65° C. After the completion of dropwise addition, the mixture was cooled to room temperature and filtrated to give the objective compound (15.74 g, yield 93.9%). Purity 98.7%.

EXAMPLE 2-2

4-Fluorothiophenol (2.79 g, 21.8 mmol) and THF (30 ml) were charged in a 100 ml four-neck flask, and the mixture was stirred under ice-cooling. 20% Aqueous NaOH solution (5.0 g, 25.0 mmol) was added dropwise thereto. 4-Cyano-N-(2,3-epoxy-2-methylpropionyl)-3-trifluoromethyl aniline (5.59 g, 20.7 mmol) was dissolved in THF (25 ml) and the solution was added dropwise at a range of 5° C.–10° C. After stirring for 2 hr, toluene (15 ml) and saturated brine (15 ml) were added and the mixture was partitioned. Saturated brine (20 ml) was added to the organic layer, and the organic layer was adjusted to pH=4 (universal test paper) with 5N HCl and washed. The mixture was dried over $MgSO_4$, decolorized with activated carbon (carborafine 0.5 g) and concentrated under reduced pressure to give a residue. Toluene (15 ml) was added to the residue and n-heptane (10 ml) was added dropwise thereto at a temperature of 70° C.–65° C. After the completion of the dropwise addition, the mixture was allowed to cool to room temperature and filtrated to give the objective compound (7.45 g, yield 90.2%). Purity 99.0%.

EXAMPLE 3
Synthesis of 4'-cyano-3-[(4-fluorophenyl)sulfonyl]-2-hydroxy-2-methyl-3'-trifluoromethylpropionanilide 4'-Cyano-3-(4-fluorophenylthio)-2-hydroxy-2-methyl-3'-trifluoromethylpropionanilide (12.20 g, 30.6 mmol) and ethyl acetate (20 ml) were successively charged in a 200 ml four-neck flask, and the mixture was stirred under ice-cooling (2° C.–7° C.). A solution of mono-perphthalic acid in ethyl acetate (166.58 g, net 22.31 g, 122.5 mmol) was dropwise added at not higher than 10° C., and the mixture was stirred for 1 hr. A 20% KOH solution (117.5 g) was dropwise added thereto and the mixture was partitioned. The aqueous layer was extracted with ethyl acetate (30 ml). The combined organic layer was washed with a solution of sodium pyrosulfite (3.0 g) dissolved in deionized water (30 ml), dried over magnesium sulfate and concentrated under reduced pressure. Ethyl acetate (66 ml) was added to the residue and the mixture was heated to 60° C. n-Heptane (40 ml) was added dropwise at a temperature of 60° C.–65° C. over 40 min. After the completion of the dropwise addition, the mixture was allowed to cool to room temperature (about 20° C.–25° C.) and filtrated to give 4'-cyano-3-[(4-fluorophenyl)sulfonyl]-2-hydroxy-2-methyl-3'-trifluoromethylpropionanilide (12.24 g, yield 91.2%). Purity 99.97%.

EXAMPLE 4
Synthesis of 4'-cyano-3-[(4-fluorophenyl)sulfonyl]-2-hydroxy-2-methyl-3'-trifluoromethylpropionanilide
(1) Synthesis of 4-cyano-N-(2,3-epoxy-2-methylpropionyl)-3-trifluoromethylaniline N-Methacryloyl-4-cyano-3-trifluoromethylaniline (15.0 g, 59.0 mmol) and ethyl acetate (15 ml) were charged in a 500 ml four-neck flask and the mixture was heated to 50–55° C. A solution of mono-perphthalic acid in ethyl acetate (130.21 g, net 21.49 g, 118.0 mmol) was added dropwise over 3.25 hr. After stirring for 2 hr at the above-mentioned temperature, a solution of mono-perphthalic acid in ethyl acetate (32.55 g, net 5.37 g, 29.5 mmol) was added dropwise over 25 min. Then the mixture was stirred for 2 hr and left standing overnight at room temperature. The mixture was adjusted to pH≅8 (universal test paper) with 20% aqueous KOH solution (100 ml), 10% $Na_2SO_3$ (45.40 g) was added to the mixture, and the solution was partitioned. The organic layer was washed with a solution of $Na_2S_2O_5$ (5.0 g) in deionized water (20 ml), dried over $MgSO_4$ and subjected to LC analysis.
—LC conditions—
mobile phase: constant composition of 0.02 M aqueous $KH_2PO_4$ solution:acetonitrile=50:50 (v/v)

| | |
|---|---|
| column | SUMIPAX ODS C-212 |
| temperature | 40° C. |
| wavelength | 254 nm |
| flow rate | 1 mL/min |

When the LC sensitivity of the objective epoxy form [4-cyano-N-(2,3-epoxy-2-methylpropionyl)-3-trifluoromethyl aniline] was 100%, that of the diol form [4-cyano-N-(2,3-dihydroxy-2-methylpropionyl)-3-trifluoromethylaniline], which was a by-product, was 5.51%.

(2) Conversion of diol form to 4-cyano-N-(2,3-epoxy-2-methylpropionyl)-3-trifluoromethylaniline The reaction mixture obtained in the above-mentioned (1) was concentrated under reduced pressure, and toluene (50 ml) was added thereto. The mixture was again concentrated under reduced pressure. Toluene (30 ml) was added thereto and the mixture was stirred under ice-cooling. MsCl (1.35 g, 11.8 mmol) and $Et_3N$ (2.39 g, 23.6 mmol) were added dropwise at not higher than 10° C. As a result of the LC analysis (under the same conditions as the above-mentioned LC conditions), the diol form was 0.32% of the epoxy form. Again, MsCl (0.36 g, 3.1 mmol) and $Et_3N$ (0.60 g, 5.9 mmol) were added dropwise at not higher than 10° C. As a result of the LC analysis (under the same conditions as the above-mentioned LC conditions), the diol form was 0.20% of the epoxy form.
(3) Synthesis of 4'-cyano-3-(4-fluorophenylthio)-2-hydroxy-2-methyl-3'-trifluoromethylpropionanilide The reaction mixture obtained in the above-mentioned (2) was cooled to 5° C. under ice-cooling. After dropwise addition of 4-fluorothiophenol (7.60 g, 59.3 mmol) at not higher than 10° C., and $Et_3N$ (2.42 g, 23.9 mmol) was added thereto. After 1 hr, 4-fluorothiophenol (0.5 ml, 0.602 g, 4.7 mmol) was added thereto. After 1 more hour, 4-fluorothiophenol (0.5 ml, 4.7 mmol) was added and the mixture was stirred overnight at room temperature. The reaction mixture was added to saturated brine (40 ml) and partitioned. Saturated brine (40 ml) was added to the organic layer, and the mixture was adjusted to pH≅3 (universal test paper) with 5N (mol/l) HCl and washed. After drying over $MgSO_4$, the mixture was concentrated under reduced pressure. Toluene (50 ml) was added to the obtained residue and the mixture was heated to 70° C. Activated carbon (carborafine, 0.5 g) and γ-alumina (1.0 g) were added, and the solution was filtered after stirring at the above-mentioned temperature for 10 min. After allowing to cool to 20° C., the mixture was filtrated to give a sulfide form [4'-cyano-3-(4-fluorophenylthio)-2-hydroxy-2-methyl-3'-trifluoromethylpropionanilide] (18.19 g). Purity 98.4%, yield 77.4% (total yield of (1) to (3)).
(4) Synthesis of 4'-cyano-3-[(4-fluorophenyl)sulfoyl]-2-hydroxy-2-methyl-3'-trifluoromethylpropionanilide Ethyl acetate (30 ml) was added to the sulfide form (18.14 g, 45.5 mmol) obtained in the above-mentioned (3), and the mixture was stirred under ice-cooling. A solution of mono-perphthalic acid in ethyl acetate (116.22 g, net 20.73 g, 113.82 mmol) was added dropwise at not higher than 5° C. After the completion of the dropwise addition, the bath was removed and the mixture was stirred overnight at room temperature. The mixture was adjusted to pH≅8 (universal test paper) with 20% aqueous KOH solution, and after partitioning, the organic layer was washed with 10% aqueous sodium bisulfite solution (60 ml) and saturated brine (60 ml). After drying over $MgSO_4$, activated carbon (0.60 g) was added and the mixture was filtrated. The mixture was concentrated under reduced pressure and ethyl acetate (20 ml) was added to the residue. The mixture was heated to 65° C., allowed to cool to 15° C. and filtrated to give 4'-cyano-3-[(4-fluorophenyl)sulfonyl]-2-hydroxy-2-methyl-3'-trifluoromethylpropionanilide (13.84 g). Yield 70.6%, purity 99.8%.

EXAMPLE 5
Synthesis of 4'-cyano-3-(4-fluorophenylthio)-2-hydroxy-2-methyl-3'-trifluoromethylpropionanilide N-Methacryloyl-4-cyano-3-trifluoromethylaniline (15.0 g, 59.0 mmol) and ethyl acetate (25 ml) were charged in a 500 ml four-neck flask and the mixture was heated at 50–55°

C. A solution of mono-perphthalic acid in ethyl acetate (160.14 g, net 21.49 g, 118.0 mmol) was added dropwise over 3.16 hr. After stirring at the above-mentioned temperature for 2 hr, a solution of mono-perphthalic acid in ethyl acetate (46.95 g, net 6.12 g, 33.6 mmol) was dropwise added over 1.5 hr and the mixture was stirred for 1.5 hr. The mixture was adjusted to pH≅8 (universal test paper) with 20% aqueous KOH solution (100 ml) and 10% Na$_2$SO$_3$ (45.40 g) was added. The mixture was partitioned, and the organic layer was washed with a solution of Na$_2$S$_2$O$_5$ (5.0 g) in deionized water (20 ml) and then dried over MgSO$_4$. When the LC sensitivity of the epoxy form is 100%, the diol form was 6.91%.

The obtained reaction mixture was concentrated under reduced pressure and then toluene (50 ml) was added thereto. The mixture was again concentrated under reduced pressure. Toluene (30 ml) was added thereto and the mixture was stirred under ice-cooling. MsCl (2.04 g, 17.7 mmol) and Et$_3$N (3.58 g, 35.4 mmol) were added dropwise at not higher than 10° C. As a result of LC analysis (under the same conditions as the above-mentioned LC conditions), the diol form was 0.37% of the epoxy form.

The obtained reaction mixture was cooled to 5° C. under ice-cooling. 4-Fluorothiophenol (9.15 g, 71.4 mmol) was added dropwise thereto at not higher than 10° C. After 1 hr, 4-fluorothiophenol (0.5 ml, 0.602 g, 4.7 mmol) was further added thereto and the mixture was stirred overnight at room temperature. The reaction mixture was added to saturated brine (40 ml) and the mixture was partitioned. Saturated brine (40 ml) was added to the organic layer, and the mixture was adjusted to pH≅3 (universal test paper) with 5N (mol/l) HCl and washed. After drying over MgSO$_4$, the mixture was concentrated under reduced pressure. Toluene (50 ml) was added to the obtained residue and the mixture was heated to 70° C. Activated carbon (carborafine, 0.5 g) and γ-alumina (1.0 g) were added, and the mixture was stirred at the above-mentioned temperature for 10 min, and then filtrated. After allowing to cool to 20° C., the mixture was filtrated to give a sulfide form (17.65 g). Purity 96.5%, yield 75.1%.

EXAMPLE 6

Synthesis of 4'-cyano-3-(4-fluorophenylthio)-2-hydroxy-2-methyl-3'-trifluoromethylpropionanilide The following reactions were carried out under a nitrogen atmosphere unless particularly specified.

N-Methacryloyl-4-cyano-3-trifluoromethylaniline (15.0 g, 59.0 mmol) and ethyl acetate (40 ml) were charged in a 500 ml four-neck flask, and the mixture was heated at 50–55° C. Nitrogen was flown at a flow rate of 10 ml/min. A solution of mono-perphthalic acid in ethyl acetate (119.4 g, net 21.5 g, 118 mmol) was dropwise added and the mixture was stirred for 2 hr. Thereafter, a solution of mono-perphthalic acid in ethyl acetate (55.7 g, net 10.0 g, 55 mmol) was dropwise added and the mixture was stirred for 4 hr. After cooling to not higher than 10° C., a 15% Na$_2$SO$_3$ solution (99.1 g) was added dropwise. Thereafter, a 20% aqueous KOH solution was added dropwise and the mixture was adjusted to pH=8.3 and partitioned. The organic layer was concentrated under reduced pressure. Toluene (50 ml) was added thereto and the solution was again concentrated under reduced pressure. THF (90 ml) was added to the residue, and after dissolution, the mixture was cooled to not higher than 10° C. Et$_3$N (2.4 g, 23.6 mmol) and MsCl (1.4 g, 12.2 mmol) were successively added dropwise thereto at not higher than 10° C. and the mixture was stirred for 30 min. Again, Et$_3$N (0.63 g, 6.2 mmol) and MsCl (0.35 g, 3.0 mmol) were dropwise added thereto at not higher than 10° C. and the mixture was stirred for 30 min. As a result of the LC analysis, a diol form was detected. Thereafter, 4-fluorothiophenol (9.12 g, 7.6 ml, 71.2 mmol) was diluted with toluene (15 ml) and the solution was added dropwise at not higher than 10° C. After stirring for 1 hr, the bath was removed and the mixture was stirred at room temperature for 2 hr. Et$_3$N (4.8 g, 47.7 mmol) was dropwise added thereto and the mixture was heated to 40° C. and stirred for 8 hr. After cooling to room temperature, saturated brine (70 ml) was added thereto and the mixture was partitioned. Saturated brine (50 ml) was added thereto and the mixture was adjusted to pH<3 (universal test paper) with 35% HCl and partitioned. The organic layer was concentrated under reduced pressure, and then toluene (60 ml) was added. After heating to 65° C., γ-alumina (0.75 g) and activated carbon (0.90 g) were added thereto and the mixture was filtrated. Thereafter, the mixture was allowed to cool to not higher than 10° C. and filtrated to give the title compound (19.71 g, yield 83.9%, yield from N-methacryloyl-4-cyano-3-trifluoromethylaniline, purity 99.4% (LC)).

EXAMPLE 7

Synthesis of 4'-cyano-3-[(4-fluorophenyl)sulfonyl]-2-hydroxy-2-methyl-3'-trifluoromethylpropionanilide Ethyl acetate (130 ml) was added to 4'-cyano-3-(4-fluorophenylthio)-2-hydroxy-2-methyl-3'-trifluoromethylpropionanilide (16.74 g, 42.02 mmol), and the mixture was stirred at 0° C. under ice-cooling. A solution of mono-perphthalic acid in ethyl acetate (116.72 g, net 19.13 g, 105.03 mmol) was added dropwise thereto at not higher than 5° C. After completion of the dropwise addition, the bath was removed and the mixture was stirred overnight at room temperature. The reaction mixture was washed with a solution of sodium bisulfite (7.94 g) in water (40 ml) and the mixture was partitioned. The organic layer was concentrated at a bath temperature of 90–95° C. and ethyl acetate (240 ml) was distilled away (distillation temperature 75–77° C.) to make the solution about 65 ml. After allowing to cool to 10° C. for 12 hr, the mixture was stirred for 40 min and filtrated to give a crystal of the title compound (15.50 g). Yield 85.7%, purity 99.56%.

EXAMPLE 8

Synthesis of 4'-cyano-3-[(4-fluorophenyl)sulfonyl]-2-hydroxy-2-methyl-3'-trifluoromethylpropionanilide Sodium tungstate dihydrate (1.48 g, 4.5 mmol), phenylphosphonic acid (356 mg, 2.25 mmol), tetrabutylammonium bromide (725 mg, 2.25 mmol) and 35% aqueous hydrogen peroxide (109.3 g, 1.125 mol) are charged in a reaction vessel, and the mixture is stirred at 15–25° C. for 30 min. A solution of 4'-cyano-3-(4-fluorophenylthio)-2-hydroxy-2-methyl-3'-trifluoromethylpropionanilide (89.63 g, 225 mmol) in ethyl acetate (225 ml) is added dropwise to the reaction mixture over 40 min. After the completion of dropwise addition, the reaction system is refluxed at a temperature of from 73° C. to 76° C. for 1 hr.

After the completion of the reaction, ethyl acetate (675 ml) as an extract solution is further added, and the mixture is stirred at 60–70° C. for 30 min. After standing still for 30 min, the aqueous layer is separated. The obtained organic layer is washed with 10% sodium sulfite (300 g) and 15% brine (300 g). Then ethyl acetate (400 ml) is concentrated at atmospheric pressure, and then cooled to 60° C. (crystals start to precipitate). Heptane (300 ml) is dropwise added to the solution at the same temperature over 35 min, and then the mixture is cooled to 20° C. The obtained crystals were collected by filtration, washed with a mixed solvent of ethyl acetate (50 ml)—heptane (30 ml), and then dried to give the title compound (89.6 g, yield 92.6%).

melting point: 192–194° C. (value in literature 191–193° C.)

HPLC purity: 99.93% (SUMIPAX ODS A-212: acetonitrile/0.1% aqueous acetic acid solution)

Magnesium sulfate (MgSO$_4$) used in the above-mentioned Reference Examples and Examples is anhydrous magnesium sulfate in every Example.

Evaluation of Crystal Polymorphism (X-Ray Diffraction (XRD))

To define the form of the crystal of bicalutamide, XRD measurement of the crystal of bicalutamide is conducted.

| Measurement conditions | |
|---|---|
| Apparatus | RIGAKU MINIFLEX (manufactured by Rigaku Corporation.) |
| Filter | Kβ filter |
| Wavelength | K$_{\alpha 1}$ |
| XG target | Cu |
| Slit | divergence slit |

As a result of XRD, the crystal of bicalutamide obtained in Example 3 was found to have peaks at 2θ of 6.2, 12.3, 19.1, 23.9, 24.7 and 31.1. The crystals of bicalutamide obtained in Example 4 and Example 7 were found to have peaks at 2θ of 12.18, 16.8, 18.9, 23.72 and 24.64.

Evaluation of Crystal Polymorphism (Solid $^{13}$C-NMR)

To define the form of the crystal of bicalutamide, solid $^{13}$C NMR measurement of the crystal of bicalutamide is conducted. The measurement conditions are shown in the following.

| Measurement conditions | |
|---|---|
| Apparatus | CMX-300 Infinity manufactured by Chemagnetics |
| Probe | ceramic probe |
| Temperature | room temperature (about 21° C.) |
| Measurement atmosphere | nitrogen gas |
| Observed nucleus | $^{13}$C |
| Observation frequency | 75.189 MHz |
| Pulse width | 4.0 μsec (90° pulse) |
| Spectrum width | 30.003 kHz |
| Observation point | 2048 |
| Observation repeat time | 11.0 sec |
| Contact time | 5.0 msec |
| Standard for chemical shift | methyl group of hexamethylbenzene (external standard: 17.35 ppm) |
| Rotation rate of probe | 10.5 kHz |
| Measurement method | VACP/MAS |

The spectrum of the crystal of bicalutamide obtained by the solid $^{13}$C NMR measurement is shown in FIG. 1. According to the production method of the crystal of bicalutamide of the present invention, it was clarified that the obtained crystal of bicalutamide had peaks of δ at 177.08, 168.16, 164.69, 142.31, 136.58, 133.09, 124.80, 118.50, 116.16, 104.68, 75.56, 67.14 and 29.23 ppm in solid $^{13}$C-NMR.

Particle Size Distribution and Mean Particle Size

The particle size distribution and mean particle size of the crystal of bicalutamide obtained according to the production method of the crystal of bicalutamide of the present invention were measured. The measurement conditions and the results are shown in the following.

| Measurement apparatus | SHIMADZU Particle Size Analyzer SALD-1100 |
|---|---|
| Particle size distribution | D$_{10}$ 9.5 μm, D$_{50}$ 30.3 μm, D$_{90}$ 65.9 μm |
| Average Particle Size | 30.3 μm |

INDUSTRIAL APPLICABILITY

According to the present invention, bicalutamide having a defined crystal form, as well as economical and industrially practical production methods of bicalutamide and a crystal thereof, which are superior in environmental benignity and safety, can be provided.

This application is based on a patent application Nos. 2001-380686 and 2002-166213 filed in Japan, the contents of which are all hereby incorporated by reference.

The references cited herein, including patents and patent applications, are hereby incorporated in their entireties by reference, to the extent that they have been disclosed herein.

What is claimed is:

1. A production method of bicalutamide represented by the formula (I):

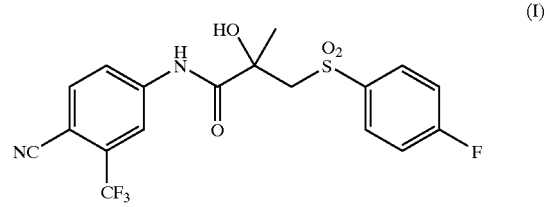

(I)

which comprises a step of reacting a compound represented by the formula (1):

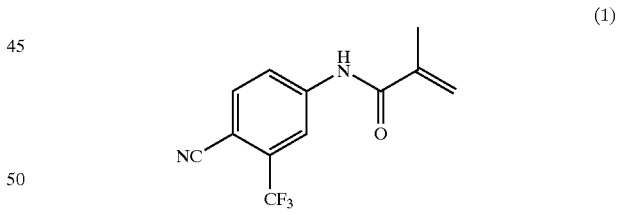

(1)

with mono-perphthalic acid to give a compound represented by the formula (2):

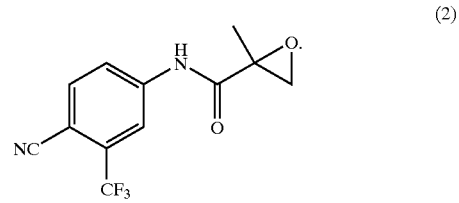

(2)

2. The production method of claim 1, further comprising use of methanesulfonyl chloride.

3. A production method of bicalutamide represented by the formula (I):

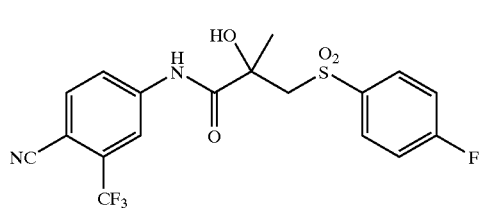

with mono-perphthalic acid.

4. A production method of bicalutamide represented by the formula (I):

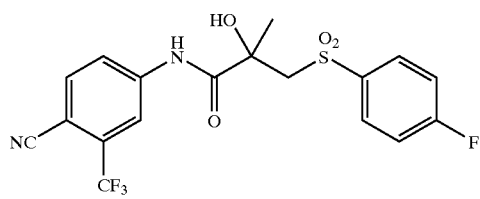

which comprises the following Steps (A)–(C):

(A) a step of reacting a compound represented by the formula (1):

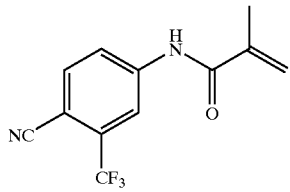

with mono-perphthalic acid to give a compound represented by the formula (2):

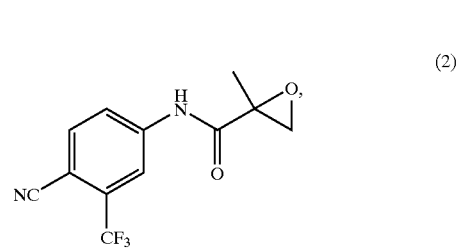

(B) a step of reacting the compound of the formula (2) obtained in Step (A) with 4-fluorothiophenol to give a compound represented by the formula (3):

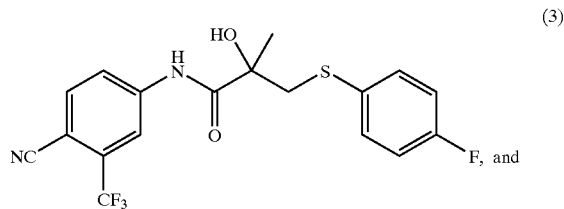

(C) a step of reacting the compound of the formula (3) obtained in Step (B) with mono-perphthalic acid to give bicalutamide.

5. The production method of claim 4, wherein Step (A) further comprises use of methanesulfonyl chloride.

* * * * *

UNITED STATES PATENT AND TRADEMARK OFFICE
CERTIFICATE OF CORRECTION

PATENT NO. : 6,740,770 B2
APPLICATION NO. : 10/362410
DATED : May 25, 2004
INVENTOR(S) : Shintaku et al.

It is certified that error appears in the above-identified patent and that said Letters Patent is hereby corrected as shown below:

Column 25,

Line 3, " 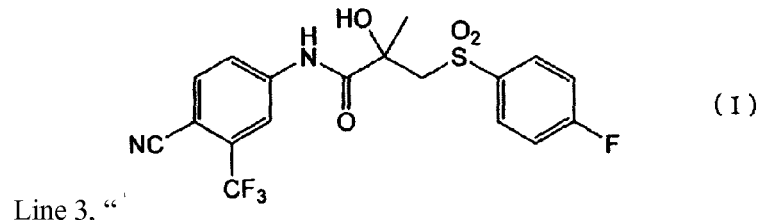 " should read

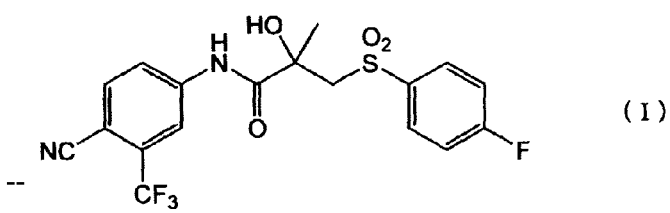

-- which comprises reacting a compound represented by the formula (3):

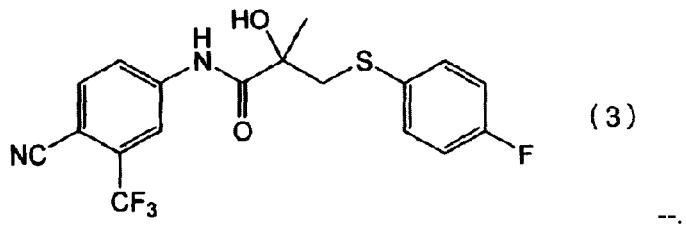

--.

Column 26,
Line 38, "wherein Step (A)" should read --wherein the Step (A)--.

Signed and Sealed this

Twenty-fourth Day of October, 2006

JON W. DUDAS
*Director of the United States Patent and Trademark Office*